US011459663B2

(12) United States Patent
Armiger et al.

(10) Patent No.: US 11,459,663 B2
(45) Date of Patent: Oct. 4, 2022

(54) ELECTROCHEMICAL BIOREACTOR MODULE AND USE THEREOF

(71) Applicant: Biocheminsights, Inc., Malvern, PA (US)

(72) Inventors: William B. Armiger, Malvern, PA (US); David R. Dodds, Manlius, NY (US)

(73) Assignee: Biocheminsights, Inc., Malvern, PA (US)

( * ) Notice: Subject to any disclaimer, the term of this patent is extended or adjusted under 35 U.S.C. 154(b) by 320 days.

(21) Appl. No.: 15/523,841

(22) PCT Filed: Nov. 2, 2015

(86) PCT No.: PCT/US2015/058560
§ 371 (c)(1),
(2) Date: May 2, 2017

(87) PCT Pub. No.: WO2016/070168
PCT Pub. Date: May 6, 2016

(65) Prior Publication Data
US 2017/0335473 A1 Nov. 23, 2017

Related U.S. Application Data

(60) Provisional application No. 62/074,065, filed on Nov. 2, 2014.

(51) Int. Cl.
*C25B 9/19* (2021.01)
*C12P 3/00* (2006.01)
(Continued)

(52) U.S. Cl.
CPC ............. *C25B 9/19* (2021.01); *C12P 1/00* (2013.01); *C12P 3/00* (2013.01); *C12Y 101/01* (2013.01);
(Continued)

(58) Field of Classification Search
CPC .... C25B 3/04; C25B 9/08; C25B 9/19; C25B 9/21; C12P 1/00; C12P 3/00; C12Y 101/01; C12Y 101/01001
See application file for complete search history.

(56) References Cited

U.S. PATENT DOCUMENTS 4,795,704 A   1/1989  Matson
6,024,855 A * 2/2000  Sharifian ............... B01D 61/44
                                                    204/522
(Continued)

FOREIGN PATENT DOCUMENTS

CN    101151764 A    3/2008
WO    02/086999 A1   10/2002
(Continued)

OTHER PUBLICATIONS

Li et al., "Advancing Membrane Bioelectrochemical Reactor (MBER) with Hollow-Fiber Membranes Installed in the Cathode Compartment," Journal of Chemical Technology and Biotechnology (Sep. 2014), vol. 89, Issue 9, pp. 1330-1336. (Year: 2014).*
(Continued)

*Primary Examiner* — Ciel P Contreras
(74) *Attorney, Agent, or Firm* — Greenberg Traurig, LLP; Fang Xie

(57) ABSTRACT

A device and process for using the device are provided for the production of commodity, specialty, performance or fine chemicals by redox enzyme systems which require the addition of reducing equivalents. The device allows operating conditions to be conveniently altered to achieve maximal electrochemical efficiencies for a given enzymatically mediated redox reaction or series of reactions.

23 Claims, 5 Drawing Sheets

(51) Int. Cl.
C25B 3/25 (2021.01)
C12P 1/00 (2006.01)
(52) U.S. Cl.
CPC ........ C12Y 101/01001 (2013.01); C25B 3/25 (2021.01)

(56) References Cited

U.S. PATENT DOCUMENTS

| | | | |
|---|---|---|---|
| 6,270,649 | B1 | 8/2001 | Zeikus et al. |
| 7,250,288 | B2 | 7/2007 | Zeikus et al. |
| 8,785,058 | B2 | 7/2014 | Iqbal et al. |
| 2003/0198859 | A1 | 10/2003 | Ritts et al. |
| 2004/0241771 | A1* | 12/2004 | Zeikus ............... C02F 3/005 435/7.32 |
| 2005/0095466 | A1 | 5/2005 | Minteer et al. |
| 2010/0105116 | A1* | 4/2010 | Datta ............... B01D 63/02 435/140 |
| 2013/0126336 | A1* | 5/2013 | Sakai ............... C25B 1/02 204/225 |
| 2014/0206896 | A1* | 7/2014 | Sivasankar ........ C07C 51/347 560/204 |
| 2015/0259669 | A1* | 9/2015 | May ................. C12N 1/20 435/135 |

FOREIGN PATENT DOCUMENTS

| | | |
|---|---|---|
| WO | 2008/058165 | 5/2008 |
| WO | 2014/039767 | 3/2014 |
| WO | 2016/070168 | 5/2016 |

OTHER PUBLICATIONS

PCT International Search Report and Written Opinion for International Application No. PCT/US15/58560, dated Feb. 2, 2016.
Sidney Aquine Neto et al., "New Energy Source: The Enzymatic Biofuel Cell", Journal of the Brazilian Chemical Society, vol. 24, No. 12, pp. 1891-1912, Jan. 1, 2013.
Bartleet, P.N., "Modified Electrode Surface in Amperometric Biosensors," Medical and Biological Engineering and Computing, May 1990, vol. 28, pp. B10-B17.
Hollmann et al., "Non-Enzymatic Regeneration of Nicotinamide and Flavin Cofactors for Monooxygenase Catalysis," Trends in Biotechnology, Apr. 2006, vol. 24, No. 4, pp. 163-171.
Hongo et al., "Application of Electro-energizing Method to L-Glutamic Acid Fermentation," Agricultural and Biological Chemistry, Oct. 1, 1979, vol. 43, No. 10, pp. 2075-2081.
Karyakin et al., "Equilibrium (NAD+/NADH) Potential on Poly(Neutral Red) Modified Electrode," Electrochemistry Communications, 2003, vol. 5, No. 8, pp. 677-680.
Kim et al., "Photogeneration of NADPH by Oligothiophenes Coupled with Ferredoxin-NADP Reductase," Journal of Biotechnology, Jan. 1998, vol. 59, No. 3, pp. 213-220.
Miyawaki et al., "Electrochemical Bioreactor with Immobilized Glucose-6-Phosphate Dehydrogenase on the Rotating Graphite Disc Electrode Modified with Phenazine Methosulfate," Enzyme and Microbial Technology, Jun. 1993, vol. 15, No. 6, pp. 525-529.
Park et al., "Utilization of Electrically Reduced Neutral Red by Actinobacillus Succinogenes: Physiological Function of Neutral Red in Membrane-Driven Fumarate Reduction and Energy Conservation," Journal of Bacteriology, Apr. 1999, vol. 181, No. 8, pp. 2403-2410.
Park et al., "Microbial Utilization of Electrically Reduced Neutral Red as the Sole Electron Donor for Growth and Metabolite Production," Applied and Environmental Microbiology, Jul. 1999, vol. 65, No. 7, pp. 2912-2917.
Park et al., "Electricity Generation in Microbial Fuel Cells Using Neutral Red as an Electronophore," Applied and Environmental Microbiology, Apr. 2000, vol. 66, No. 4, pp. 1292-1297.
Park et al., "Electricity Production in Biofuel Cell Using Modified Graphite Electrode with Neutral Red," Biotechnology Letters, 2000, vol. 22, No. 16, pp. 1301-1304.
Roberts et al., "Some Recent Advances In The Synthesis Of Optically Pure Fine Chemicals Using Enzyme-Catalyzed Reactions In The Key Step," Chimica Oggi, Jul./Aug. 1993, pp. 93-104.
Shin et al., "Evaluation of an Electrochemical Bioreactor System in the Biotransformation of 6-Bromo-2-Tetralone to 6-Bromo-2-Tetralol." Applied Microbiology and Biotechnology, 2001, vol. 57, No. 4, pp. 506-510.
Van Der Zee et al., "Impact and Application of Electron Shuttles on the Redox (Bio)Transformation of Contaminants A Review." Biotechnology Advances, May 2009, vol. 27, No. 3, pp. 256-277.
Walsh et al., "Design and Performance of Electrochemical Reactors for Efficient Synthesis and Environmental Treatment. Part 1. Electrode Geometry and Figures of Merit." Analyst, 1994, vol. 119, pp. 791-796.

* cited by examiner

ELECTROCHEMICAL BIOREACTOR MODULE AND USE THEREOF

CROSS REFERENCE TO RELATED APPLICATIONS

This application is a U.S. National Phase application under 35 U.S.C. 371 of International Application No. PCT/US2015/058560, filed Nov. 2, 2015, which claims priority to and the benefit of U.S. Provisional Application No. 62/074,065 filed Nov. 2, 2014, the disclosure of each of which is incorporated herein by reference in its entirety.

TECHNICAL FIELD

The present disclosure relates generally to the use of biologically mediated reactions that alter the oxidation state of compounds, and specifically the oxidation state of carbon atoms in a given chemical compound. More specifically, the present disclosure relates to an improved Electrochemical Bioreactor Module (EBM) and use thereof to manufacture desired products.

BACKGROUND

In the context of chemical reactions, a reduction is the gaining of an electron by a particular chemical species and an oxidation is the loss of an electron from a particular chemical species. The general term "redox" reaction is short for oxidation-reduction reaction. A redox reaction is one which involves the transfer of electrons from one chemical species to another. Electrochemical cells are defined as systems that utilize a combination of redox reactions either to produce useful electrical energy, or use electrical energy to drive a combination of useful redox reactions (Silberberg, Martin (2009) *Chemistry: The Molecular Nature of Matter and Change* (5$^{th}$ Ed.) New York, N.Y.: McGraw-Hill).

An electrochemical cell contains two electrodes known as the anode and the cathode. The transfer of electrons from an electrode to a chemical species, that is a reduction reaction, occurs at the cathode, and the transfer of electrons from a chemical species to an electrode, that is, an oxidation reaction, occurs at the anode. In order to balance the depletion of electrons at the cathode, and the accumulation of electrons at the anode, electrons must flow from the anode to the cathode in some manner outside of the electrochemical cell, i.e., through a wire or some other material that allows the movement of electrons. This flow of electrons is an electrical current, and may be harnessed to perform work e.g. drive an electrical device. Conversely, the flow of electrons from anode to cathode may be driven by an external power source, such as a battery or electromotive force (EMF), causing a useful chemical reaction to occur at either the anode or the cathode, or both.

An electrochemical cell can be constructed either to generate an electrical current, that is, a unidirectional flow of electrons through a conductive element such as a wire, from spontaneous redox reactions that occur at the anode and the cathode, or it can be constructed to consume electrical current provided by an external source, such as a battery or EMF, to drive non-spontaneous reactions at the anode and cathode. In the latter case, the electrically-driven, non-spontaneous reactions may be termed electrosynthesis.

An electrochemical cell requires two reactions to occur, one at the anode and one at the cathode, the reactions occurring at each electrode are termed half-cell reactions, or half-reactions. Regardless of whether an electrochemical cell is consuming or generating an electrical current, half-cell reactions are necessarily occurring simultaneously at both the anode and the cathode.

Half-cell reactions are considered to have a positive or negative reduction/oxidation potential, termed redox potential; this is the equilibrium constant between the oxidized and reduced species of the half-cell reaction expressed in volts and relative to the dissociation of hydrogen to protons and electrons, which is considered to have a redox potential of zero volts.

Conditions under which the redox potential of the environment is more positive than the redox potential of a given half-cell reaction will force the half-cell reaction towards the oxidized species of the reaction. Conditions under which the redox potential of the environment is more negative than the redox potential of a given half-cell reaction will force the half-cell reaction towards the reduced species of the half-cell reaction.

By supplying electrons from an external source, i.e., applying a negative voltage from an external power supply (e.g., a battery) to the cathode of an electrochemical cell, the redox potential of the environment around the cathode can be made more negative. This effect can be used to force half-cell reactions to generate the reduced species. To balance this, a half-cell reaction must necessarily be occurring at the anode at the corresponding positive voltage, thus forcing the half-cell reaction at the anode to proceed to the oxidized species.

Thus, electrons provided to the environment in the cathode chamber of an electrochemical cell will cause half-cell reactions to produce reduced species from a substrate.

Any reaction which leads to a reduction or oxidation of a particular chemical species may provide a useful half-cell reaction. This includes living systems in which the desired half-reactions are present in metabolic pathways that perform the conversion of organic compounds and are catalyzed by enzymes. As previously noted, the half-cell reactions are generally termed redox reactions; hence the enzymes which catalyze such half-reactions are generally termed redox enzymes. Typically, but not exclusively, redox enzymes require other biological components termed co-enzymes or co-factors, and it is these co-enzymes or co-factors which physically transport electrons between the various redox enzymes which catalyze the half-cell reactions (redox reactions) in a given biological system.

In order for redox enzymes to catalyze redox reactions, the co-factors or co-enzymes must be in the appropriately oxidized or reduced form. In living cells, this is accomplished in metabolic processes. In order to oxidize a given carbon atom, the metabolic processes of the micro-organism or other cells must remove electrons from the carbon atom of interest, and in order to reduce a given carbon atom, the metabolic processes must provide electrons to the carbon atoms of interest.

In the case of oxidation, this is easily achieved by using molecular oxygen from the environment (e.g., from air) as a "sink" for electrons, and in the process, the oxygen molecule is electrochemically reduced, typically producing two water molecules.

In the case of reduction, the metabolic processes in the micro-organism must oxidize some other chemical species to provide electrons for performing the desired reduction. Most commonly in the case of micro-organisms growing on a carbon source such as a carbohydrate, reducing equivalents are generated by completely oxidizing a portion of the carbohydrate to $CO_2$, that is, some of the carbohydrate provided to the micro-organism is sacrificially oxidized in order to provide electrons for the micro-organism to use in metabolic processes that produce organic molecules that are more reduced. While the resulting electrons are desirable and useful to the microorganism, the carbon atoms sacrificed by oxidation to $CO_2$ are lost.

Similar calculations will apply to all metabolic processes which sacrifice some of the input carbonaceous material in order to provide electrons for desired metabolic processes.

If electrons could be provided from an external source, that is, an electrical current, then the need to sacrifice input carbonaceous material to provide electrons would be eliminated, and individual redox enzymes could be used as conventional catalysts, performing redox reactions without the need for living cells and associated biological systems or processes, such as active fermentations.

Significantly improved chemical processes could be achieved by a system which allowed the use of the plethora of redox enzymes in processes resembling standard catalytic chemical processes. Removing the aspect of an actively metabolizing cell in a fermentation broth would permit higher concentrations of substrate to be used, non-physiological conditions, and ease of isolation and purification of the desired product. For example, the use of electrochemical methods to regenerate the flavin adenine dinucleotide (FAD) cofactor for the P450 mono-oxygenase which catalyses the Bayer-Villiger oxidation has been reported (Schmid et al, *J. Am. Chem. Soc.* 2005, 127, 6540-6541), although this was in a 10 mL volume contained in a simple stirred flask. However, no attempt to perform the reaction at a scale practical for industrial purposes was described.

Micro-organisms containing useful redox enzymes are widely known in nature and can be found quickly by simple screening. If a particular redox enzyme is required and the native host organism is not easily grown or handled, the redox enzyme can be readily cloned and over-expressed in a standard industrially useful host such as *S. cerevisiae* or *E. coli*.

It is thus highly desirable to provide electrons from an external source to redox enzyme system in a physical arrangement that allows a substrate molecule to be provided in a continuous process stream, a desired redox reaction to be catalyzed by a chosen redox enzyme, and the resulting product easily recovered and isolated from a continuous process stream.

This desire has been recognized by others, and a number of attempts to deliver electrons to biological systems have been published. The transfer of electrons from an electrode (the cathode) to a biological system, is also improved by the use of electron transport mediators, and the compound neutral red (NR) enjoys general use in this regard.

U.S. Pat. No. 6,270,649 to Zeikus et al. shows that neutral red is an improved electron mediator for either converting electricity into microbial reducing power for enhanced cell growth and production of reduced end-products (see, Park et al., *Appl. Environ. Microbioi.* 65:2912-2917, 1999; and Park et al., *J. Bacteriol.* 1812:2403-2410, 1999), or converting microbial reducing power into electricity in biofuel cells (see, Park and Zeikus, *Appl. Environ. Microbiol.* 66:1292-1297, 2000).

Park et al., in *J. Bacteriol.* 1812:2403-2410, 1999, provides the first biochemical evidence of how NR functions physiologically by showing that (i) the electrical reduction of NR is chemically linked to NAD+ reduction and that it is biochemically linked to generation of a proton motive force and succinate production and (ii) that NR appears to function by replacing menaquinone in the membrane-bound complex.

Park et al. in *Biotech. Lett.* 22: 1301-1304, 2000, showed that binding neutral red to a graphite electrode further enhanced electron transfer efficiency in microbial fuel cells.

The electrical enhancement of fermentations and biotransformations also involves the utilization of an electrode and electron mediator in a bioreactor system to enhance the production of reduced end products (see, Hongo et al., *Agri. Biolio. Chem.,* 43: 2075-20811 1979; Hongo et al., *Agri. Biolio. Chem.,* 43: 2083-2086, 1979; Kim et al., 1988; Park and Zeikus, *J. Bacteriol.* 181: 403-2410, 1999; and Shin et al., *Appl Microbiol Biotechnol.,* DOI 10.1007/s002530100809. Online publication: Sep. 22, 2001.) For example, a graphite felt electrode and soluble neutral red can greatly enhance the yields of succinate produced by fermentation (see Park and Zeikus, *J. Bacteriol.* 181: 403-2410, 1999) and, tetralol produced by yeast transformation (Shin et al., *Appl Microbiol Biotechnol.,* DOI 10.1007/s002530100809. Online publication: Sep. 22, 2001).

One major factor limiting the utilization of oxidoreductases in chemical syntheses (see, e.g., S. M. Roberts et al., *Chimicaoggi,* July/August 1993, pp. 93-104; and D. Miyawaki et al., *Enzg. Microbiol. Technol.* 15:525-29, 1993) or in chemical detection, i.e., biosensors (see, e.g., P. N. Bartlett, *Med. And Biol. Eng. and Comput.* 28: BIO-B7, 1990; and D. Miyawaki et al., supra) is the lack of a facile system for regeneration or recycling of the electron transferring cofactors (e.g., nicotinamide adenine dinucleotide, quinones, flavin adenine dinucleotide, etc).

While electrons may be transported by co-factors in biological systems as single electrons, transport of electrons frequently occurs as pairs of electrons. In the case of pairs of electrons, a proton is also formally transported, and the formal chemical species is thus a hydride, that is, a hydrogen atom bearing an additional (second) electron and hence a negative charge, and generally written as "H$^-$".

Within biological systems, such species are historically termed "reducing equivalents", as the formal addition of hydride to a chemical species results in a reduction of that chemical species. Formally, an additional, second proton is required to neutralize the formal negative charge that the reduced product of the reaction would carry through addition of the hydride species. Most commonly in biological systems, the necessary protons are provided simply via hydronium ions (i.e. a protonated water molecule, $H_3O^+$). Within an electrochemical cell, protonated water molecules may be generated at the anode and allowed to migrate to the cathode.

It has been reported by Park and Zeikus in *J. Bacteriol.* 181:2403-2410, 1999 that the compound called Neutral Red would undergo reversible chemical oxidoreductions with the nicotinamide adenine dinucleotide cofactor (NAD+) that is, Neutral Red in its reduced form ($NR_{red}$) has a sufficiently low redox value that it will transfer electrons to, and thus reduce, the redox cofactor NAD+ from its oxidized form to its reduced form NADH. In this process, neutral red becomes oxidized to the species $NR_{ox}$ which is then available to accept an electron from the cathode and thus return to the reduced form $NR_{red}$, which is in turn available to reduce NAD+.

It has also been reported that by using soluble Neutral Red in electrochemical reactors containing microbes that: microbes could grow on electricity alone; diverse microbes could over-produce a variety of reduced biochemicals during fermentations of biotransformations; and that microbes could generate electricity during metabolism of organic matter. (See, e.g., Park et al., "*Appl. Environ. Microbioi.* pp.

2912-2917, 1990; Park and Zeikus, *Appl. Environ. Microbiol.*, 66:1292-1297, 2000; and U.S. Pat. No. 6,270,649).

U.S. Pat. No. 7,250,288 B2 to Zeikus et al. discusses the need for improving electrode efficiencies in electrochemical bioreactor system and proposes improvements such as linking nicotinamide adenine dinucleotide ($NAD^+$), neutral red, and fumarate reductase to the electrode in order to improve electron transfer characteristics. While the above may improve electron transfer characteristics, it may also be advantageous to improve upon electrode design and electrochemical bioreactor system design in other ways.

The literature on commercial-scale electrochemical process equipment used in the production of chlorine, ozone and hydrogen peroxide documents that the scale of electrodes used in laboratory electrochemistry research often has poorly defined fluid flow and mass transport characteristics, and provides scale-up challenges (Walsh, F., and G. Reade, *Analyst,* 119 (1), pp. 797-803 (May 1994)).

Providing reducing equivalents to a microorganism can be accomplished by regenerating NADH. The standard potential is often reported in the literature as −0.32V, however according to Karyakin et al. a potential of −0.59V at pH 6 may be more accurate (see Karyakin et al., *Electrochemistry Communications* 5: 677-680, 2003).

Reduced electron shuttles can transfer electrons to several distinct electron-withdrawing compounds, such as azo dyes, polyhalogenated compounds, nitroaromatics and oxidized metalloids. Van der Zee and Cervantes review the results of reductive biotransformation process catalyzed by electron shuttles (see Frank P. Van der Zee and Francisco J. Cervantes. *Biotechnology Advances* 27: 265-277, 2009).

In order for electrochemical bioreactors to become commercially viable a change in the hardware design and processes design of the conventional systems must take place in order to improve yield and efficiencies to practical levels.

Further, while others have previously recognized the desirability of providing external electrons to biological systems, the methods revealed for accomplishing this in the examples provided therein require the anode to be contained in a manner that will prevent it from undergoing undesired reactions with the bulk biological system. Thus, some physical arrangement must be made to provide electron transfer to the anode, while keeping the anode physically separate from the fermentation broth (in the case of whole cells) or a buffer system (in the case of isolated enzymes in aqueous medium), and this is done with a variety of membranes, salt bridges or other physical means. Simplifying the design of the electrochemical cell relative to previously revealed designs, and further, designing a cell for use in a continuous, flow-through system (such as a loop running through a large fermentation vessel or chemical reactor) is desirable. It is even more desirable to arrange the electrochemical cell in a manner that utilizes a simple half-reaction at the anode, and that operates in a manner to avoid the use of salt-bridges for connectivity of the anode and cathode chambers, and mitigates membrane fouling when a membrane is used to separate the anode and cathode chambers.

It is an object of the disclosure to provide improved methods and systems that allow the interconversion of biochemical reducing power (e.g., NADH) and electrical energy in an electrochemical bioreactor module (EBM). It is a further object of the disclosure to manufacture a desired product that requires reducing power or reducing equivalents in an EBM. Another object of the present disclosure is to disclose the use of enzymes, cofactors and/or electron transport mediators in conjunction with the EBM for the purpose of manufacturing a desired product, and to do so in a process that efficiently utilizes enzymes, cofactors and/or electron transport mediators, and to substantially prevent their mixing or entrainment with the manufactured desired product.

Other objects, features, and advantages of the present disclosure will be apparent on review of the specification and claims.

SUMMARY

Figure 1:
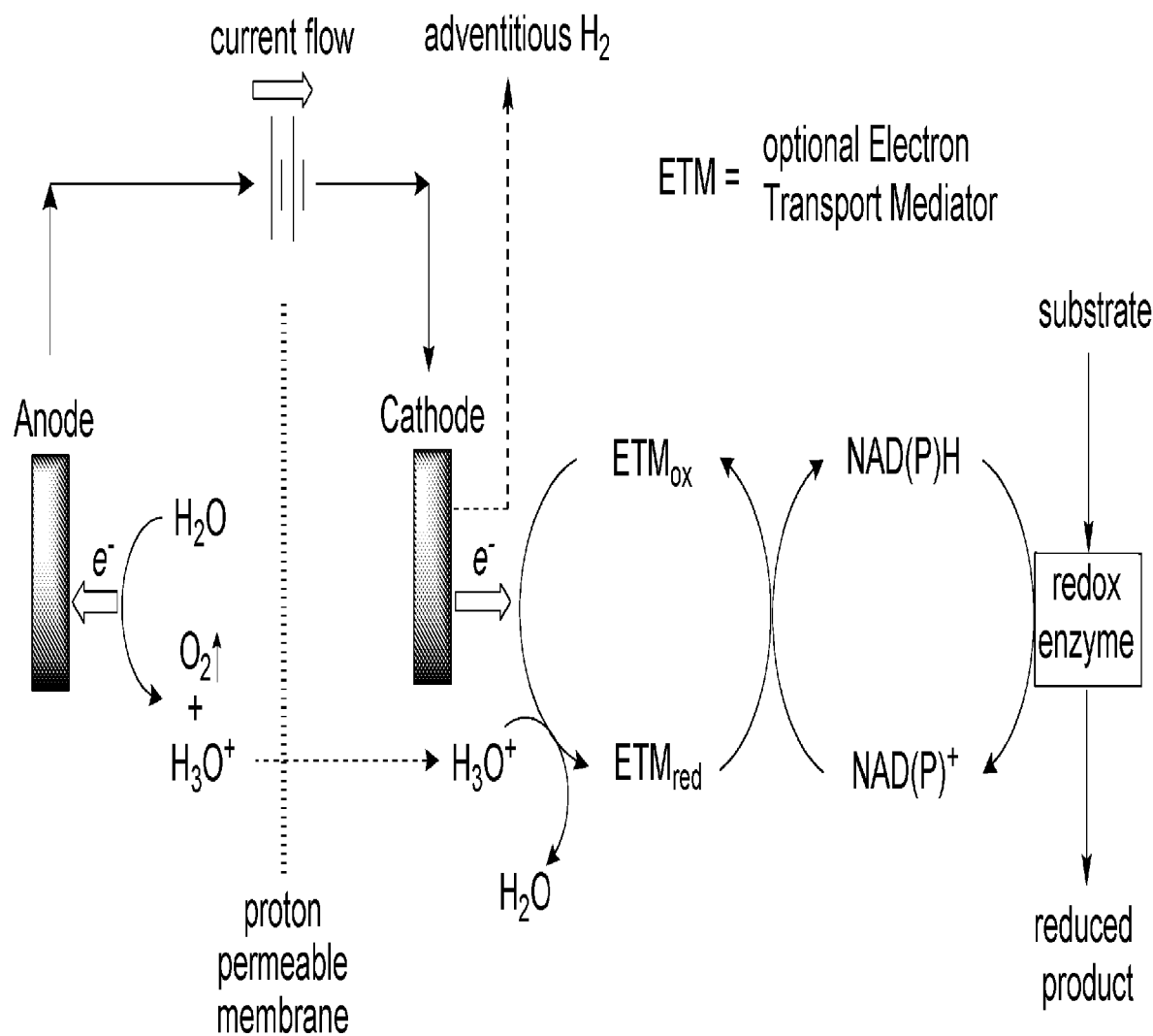
FIG. 1 illustrates, in an exemplary design, the overall electrochemistry and general arrangement of the electrochemical cell described in WO2014039767.

The present disclosure, in one aspect, includes a device or apparatus used to provide electrochemically generated reducing power or reducing equivalents to a redox enzyme for the purpose of catalyzing a desired reduction of a substrate molecule. By providing electrochemically generated reducing equivalents, this disclosure allows the use of redox enzymes in a non-physiological or non-cellular environment, and permits the use of such enzymes in industrial processes.

The device further allows the system of an electron transport mediator (ETM), a known biological cofactor such as NAD(P), and one or more redox enzymes to be contained in a manner that allows the desired substrate molecule to be provided to the device in a continuous process stream, the process stream to be contacted by the desired redox enzyme to catalyze a desired redox reaction, and the resulting desired product molecule to leave the device in a continuous process stream.

The device further allows the capture of any hydrogen gas which may be adventitiously generated at the cathode surface during the process of providing reducing equivalents to the redox enzyme.

One aspect of the present disclosure relates to a device for producing a product via a reaction requiring reducing equivalents, comprising:
  (a) an anode contained in an anode chamber and a cathode contained in a cathode chamber;
  (b) deionized water in the anode chamber in contact with the anode;
  (c) a proton permeable membrane that separates the anode and cathode chambers;
  (d) a liquid phase in the cathode chamber continuously in contact with the cathode, said liquid phase optionally comprising an electron transfer mediator (ETM) capable of transferring reducing equivalents to a redox enzyme system, said redox enzyme system comprising a redox enzyme and a cofactor;

(e) a process stream containing a substrate to be catalyzed by the redox enzyme system into a desired product;

(f) a membrane located between the cathode and the process stream, said membrane capable of preventing the optional ETM and the redox enzyme system from significantly entering into the process stream; and (g) an external power source providing a voltage between the anode and the cathode.

In some embodiments, the membrane permits interfacial contact between the liquid phase and the process stream, while preventing substantial mixing of the liquid phase and the process stream and preventing the process stream from substantially contacting the cathode. The membrane can be a hydrophilic asymmetric membrane having at least a portion of the redox enzyme system (e.g., one or more redox enzymes and optionally one or more cofactors) contained therein. The membrane can, in certain embodiments, have one or more pores extending therethrough, and the at least a portion of the redox enzyme system can be contained within the pores. The pores can have a first opening on a first surface of the membrane facing the cathode, wherein the first opening is sufficiently small to prevent molecules having a molecular weight greater than 100 KDa (e.g., greater than 100 kDa, greater than 80 kDa, greater than 60 kDa, greater than 50 kDa, greater than 40 kDa, greater than 30 kDa, greater than 20 kDa, greater than 20 kDa, greater than 10 kDa, or greater than 5 kDa) from substantially passing through. The pores can further have a second opening on a second surface of the membrane facing the process stream, wherein the second opening is sufficiently big to permit the at least a portion of the redox enzyme contained within the pores to contact the substrate in the process stream. The second opening can be larger in size than the first opening.

The co-factor can be, in some embodiments, located in the membrane or in the liquid phase.

In some embodiments, the process stream can be a bulk organic phase in which the redox enzyme system is substantially insoluble. Where the membrane is hydrophilic, the redox enzyme and/or cofactor is present in an aqueous environment which can be substantially immiscible with the bulk organic phase.

The liquid phase optionally may be recirculated in and out of the cathode chamber. The optional ETM can be selected from one or more of Neutral Red, nicotinamide adenine dinucleotide (NAD+), nicotinamide adenine dinucleotide phosphate (NADP+), flavin mononucleotide (FMN), flavin adenine dinucleotide (FAD), ferredoxin, quinone, and humic acid, each optionally chemically modified in a manner to retain their redox properties and functional interaction with redox enzymes while permitting the membrane to prevent the ETM from substantially entering into the process stream. In one embodiment, the ETM is formate or bicarbonate.

The redox enzyme system comprises, in one embodiment, a P450 enzyme, a P450 reductase, and optionally ferredoxin. In another embodiment, the redox enzyme system comprises a ketoreductase or an alcohol dehydrogenase with the necessary cofactor, most typically NAD(P). In another embodiment, the redox enzyme system is capable of catalyzing denitrification. Those skilled in the art will recognize other redox enzyme systems may be used which require the reduced form of cofactors.

Another aspect of the present disclosure relates to a method of producing a desired product from a substrate, comprising;

(a) providing any embodiment of the device disclosed herein with the process stream containing the substrate;

(b) applying a suitable voltage from the external power source between the anode and the cathode;

(c) accumulating the desired produce in the process stream; and (d) optionally, collecting an adventitiously produced hydrogen gas.

In some embodiments, the method can further comprise retaining the redox enzyme system and the optional ETM by the membrane, such that the process stream is substantially free of the redox enzyme system or the optional ETM.

DETAILED DESCRIPTION

A device and process for using the device are provided herein for the production of commodity, specialty, performance or fine chemicals by redox enzyme systems which require the addition of reducing equivalents. The device allows operating conditions to be conveniently altered to achieve maximal electrochemical efficiencies for a given enzymatically mediated redox reaction or series of reactions.

The present disclosure, in some embodiments, is directed to an improved version of the "Electrochemical Bioreactor Module" (EBM) previously described in PCT Patent Application Publication No. WO2014039767A1. The prior EBM is shown in FIG. 1, and generally comprises an electrochemical cell with an anode contained in an anode chamber, a cathode contained in a cathode chamber, a proton permeable membrane separating the two chambers, an optional ETM and a redox enzyme system. The redox enzyme can be used to catalyze reduction of a substrate into a desired product. In FIG. 1, the net flux of protons, as hydronium ions ($H_3O^+$) from the anode chamber (the "deionized water side") to the cathode chamber (the "reaction side") is indicated, together with external driven current flow and the electrochemical species. FIG. 1 shows a general Electron Transport Mediator (ETM) that is cycled between its oxidized and reduced states by accepting electrons from the cathode and delivering electrons to the NAD(P) cofactor. The ETM is optional as it is possible to deliver electrons from the cathode directly to the NAD(P) cofactor.

In some embodiments, the present disclosure relates to the use of one or more membranes in an EBM for containment of electron transport mediators (optional), redox cofactors and/or enzymes, and separation thereof from the bulk chemical reaction phase in which a substrate is catalyzed by the redox enzyme into a reduced product.

More particularly, the redox enzymes, their corresponding cofactors and optional electron transport mediators can be, in certain embodiments, separated from the bulk reaction phase by a membrane, which prevents them from substantially entering the bulk reaction phase. This way, the reaction phase is substantially free from contamination by the redox enzymes, cofactors and/or the optional electron transport mediators, significantly saving the time and cost associated with purifying the end product. In certain embodiments, the membrane can be designed to have pores in which the redox enzymes, cofactors and/or the optional electron transport mediators can be contained or located, thereby increasing the contact area of the redox enzyme with the substrate in the reaction phase and decreasing the amount of the redox enzymes, cofactors and/or the optional electron transport mediators required to promote reducing of the substrate into a desired product.

As used herein, a "redox enzyme" is an enzyme catalyzing a reaction that results in a change of chemical oxidation state of the molecule being acted upon, such molecule being termed the "substrate". In the course of the reaction, the substrate molecule accepts electrons via the redox enzyme to produce a molecule that is more chemically reduced than the substrate molecule. This reduced molecule is the "reduced product", or more simply, the "product". Exemplary products include commercially or industrially important products, such as succinic acid (reduced from, e.g., fumarate), methane (reduced from, e.g., $CO_2$), butanediol, ethanol, fatty acids and other alcohols.

The electrons, which are balanced by protons, are termed "reducing equivalents" or "reducing power". The reducing equivalents are generally provided to the redox enzyme via a cofactor. Generally, a redox enzyme and its corresponding cofactor combination that together catalyze the transformation of a substrate into a product molecule having a different chemical oxidation state is termed a "redox enzyme system".

Any suitable redox enzyme may be used in the matrices of the present invention, including mixtures of redox enzymes. The redox enzyme can be obtained from commercial sources, or be prepared via genetic engineering where a recombinant protein can be produced in larger quantities.

One example of a redox enzyme system operating on substrate molecule to give a reduced product is the reduction of a ketone to a secondary alcohol, catalyzed by an enzyme termed an "alcohol dehydrogenase" (e.g., enzyme class EC 1.1.5 in particular EC 1.1.5.2, or EC 1.1.1 in particular EC 1.1.1.1 or EC 1.1.1.2) or a "ketoreductase"; the terms in some embodiments are used synonymously. This class of enzymes is capable of acting on a >CH—OH group to oxidize it to a >C=O group (or the reverse reaction). By using a redox enzyme to catalyze this reaction, the secondary alcohol product can be produced with a desired stereochemistry or chirality. This provides considerable value to the production of pharmaceutically useful molecules, for example, in which chirality is generally an essential property.

In one embodiment, the alcohol dehydrogenase (ADH) is obtainable or is obtained from a living organism. Suitable ADH's are of bacterial or fungal origin. Preferred are ADH enzymes of bacterial origin, especially Pseudogluconobacter sacchoroketogenes ADH, *Lactobacillus* kefir ADH, Thermoanaerobium brockii ADH and *Escherichia coli* ADH, or an alcohol dehydrogenase having at least 70%, for example at least 75%, such as at least 80%, preferably at least 85%, more preferably at least 90%, even more preferably at least 95%, still more preferably at least 96%, such as at least 97%, yet more preferably at least 98%, and most preferably at least 99%, sequence identity to any thereof. Particularly preferred is Pseudogluconobacter saccharoketogenes ADH or an alcohol dehydrogenase enzyme having at least 70%, for example at least 75%, such as at least 80%, preferably at least 85%, more preferably at least 90%, even more preferably at least 95%, still more preferably at least 96%, such as at least 97%, yet more preferably at least 98%, and most preferably at least 99%, sequence identity thereto. Among ADH enzymes of fungal origin, *Saccharomyces cerevisiae* ADH, or an alcohol dehydrogenase enzyme having at least 70%, for example at least 75%, such as at least 80%, preferably at least 85%, more preferably at least 90%, even more preferably at least 95%, still more preferably at least 96%, such as at least 97%, yet more preferably at least 98%, and most preferably at least 99%, sequence identity thereto, is preferred.

Another example of a redox enzyme is the P450 monooxygenases or P450 enzymes, a class of enzymes that catalyzes a wide range of useful chemical transformations. P450 enzymes require reducing equivalents, although the product of the reaction they catalyze is actually an oxidation in which the product is more chemically oxidized than the starting substrate. To achieve this, the P450 redox enzyme uses a molecule of oxygen, $O_2$, and splits it into its two component oxygen atoms. One of the oxygen atoms is reduced to water, $H_2O$, by the reducing equivalents provided by the P450 by its cofactors, most usually a "p450 reductase" and in some cases a ferredoxin molecule. The other oxygen atom is formally inserted into an otherwise unactivated carbon-hydrogen or carbon-carbon bond, resulting in the oxidized product molecule. This type of reaction, the oxidation of unactivated carbon, is extremely difficult to perform without using a P450 enzyme, and is highly valuable as a result. A specific example is the hydroxylation reaction necessary for the production of corticosteroids. Thus providing a system in which reducing equivalents can be provided to a P450 enzyme is of considerable practical value. Although the desired product molecule is more oxidized than the substrate molecule, in the context of this disclosure it is still considered the "product", and will be present in the process stream.

Any cytochrome P450 enzyme can be used. As such, the P450s encompassed by the present disclosure include prokaryotic, eukaryotic, bacterial and mitochondrial enzymes. Cytochrome P450 (often abbreviated as CYP, P450, and infrequently CYP450) is a very large and diverse superfamily of hemoproteins which form part of multicomponent electron transfer chains, called P450-containing systems. Known cytochrome P450s amenable to the disclosure include the CYP1 family (CYP1A1; CYP1A2; CYP1B1), the CYP2 family (CYP2A6; CYP2A7, CYP2B6, CYP2A13; CYP2B6; CYP2C8; CYP2C9; CYP2C18, CYP2C19; CYP2D6; CYP2E1; CYP2F1; CYP2J2; CYP2R1; CYP2S1; CYP2U1, CYP2W1), the CYP3 family (CYP3A4; CYP3A5; CYP3A7; CYP3A43), the CYP4 family (CYP4A11; CYP4A22; CYP4B1; CYP4F2, CYP4F3, CYP4F8, CYP4F11, CYP4F12, CYP4V2, CYP4Z1), CYP5A1, CYP7A1, CYP7B1, CYP8A1, CYP8B1, CYP11A1, CYP11B1, CYP11B2, CYP17A1, CYP19A1, CYP20A1, CYP21A2, CYP24A1, CYP26A1, CYP26B1, CYP26C1, CYP27A1, CYP27B1, CYP27C1, CYP39A1, CYP46A1, and CYP51A1. Other P450s are reviewed by Urlacher and Girhard, Trends in Biotechnology, 30(1), 2012, pages 26-36, which is incorporated herein by reference in its entirety.

As used herein, the term "electron transfer mediator" or "ETM" means a molecule capable of accepting one or more electrons itself, and then transferring electrons to another molecule, including the transfer of electrons to an enzyme molecule. A typical and well known ETM is Neutral Red, which is also used as a pH indicator. Other compounds that can function as an ETM include Methylene Blue, Methyl Viologen, and quinone. Most generally, and compound whose reduction potential is more negative than that of NAD+ can be used, and this includes a variety of compounds generally termed redox dyes. For example, in the situation previously described, the Neutral Red is acting as an electron transport mediator by facilitating the movement of electrons from the cathode to the NAD+ cofactor, thus facilitating the reduction of the NAD+ to produce NADH.

The term "electron transport mediator" or "ETM" can include molecules that facilitate the transfer of electrons to an enzyme molecule, thus in a broad sense cofactors (e.g., NADH, FMN, FAD, ferredoxin, etc.) may also be considered an electron transfer mediator. However, in some examples, the term "electron transport mediator" or ETM is meant to describe only those molecules which facilitate the transfer of electrons, but which are not otherwise generally considered to be the naturally occurring cofactors of redox enzyme systems, for example, NADH, FMN, FAD, ferredoxin and the like.

In the context of the present disclosure, ETMs are generally considered desirable for facilitating the transfer of electrons from the actual cathode surface to the cofactors of redox enzyme systems. However, the cofactors of redox enzyme systems can themselves be capable of accepting electrons directly from the surface of the cathode without mediation by an ETM molecule. Thus, in the general case, the use of an ETM is optional, although will be preferred in some embodiments of the present disclosure.

In addition to providing reducing equivalents, the present disclosure allows the containment of the enzyme, NAD(P) cofactor, and the optional ETM in close proximity to the cathode by use of a suitable membrane. This arrangement prevents loss of the enzyme, NAD(P) cofactor, and the optional ETM into the much larger bulk reaction phase containing the substrate and product, thus reducing the amounts of these reagents needed and therefore reducing cost. Further, such containment of the enzyme, the cofactor, and the optional ETM, prevents them from contaminating the product in the bulk organic reaction phase, thus significantly simplifying the recovery and purification of the reduced product. This is especially useful if the ETM is a redox dye molecule.

In one aspect, a device for producing a desired product via a reaction requiring reducing equivalents is provided. The device includes:

(a) an anode contained in an anode chamber and a cathode contained in a cathode chamber;
(b) deionized water in the anode chamber in contact with the anode;
(c) a proton permeable membrane that separates the anode and cathode chambers;
(d) a liquid phase in the cathode chamber continuously in contact with the cathode, said liquid phase optionally comprising an electron transfer mediator (ETM) capable of transferring reducing equivalents to a redox enzyme system, said redox enzyme system comprising a redox enzyme and a cofactor;
(e) a process stream containing a substrate to be catalyzed by the redox enzyme system into a desired product;
(f) a membrane located between the cathode and the process stream, said membrane capable of preventing the optional ETM and the redox enzyme system from significantly entering into the process stream; and
(g) an external power source providing a voltage between the anode and the cathode.

In the present disclosure, the anode may be any convenient design that allows useful current densities. Most typically, the anode will be a titanium substrate coated with platinum. Such anode designs are now commercially available and used in electrolyzers.

The anode chamber may be any convenient design that allows the input, recirculation, and temperature control of deionized water while simultaneously allowing the output, and optionally the collection, of gas generated at the anode surface, i.e., oxygen.

In an embodiment or method of use, the anode chamber is filled with deionized water, and a sufficient voltage is applied to cause the electrolytic cleavage of water. This results in the formation of oxygen gas in the anode chamber, which may be released to the atmosphere or captured for other use. The hydronium ions ($H_3O^+$) concomitantly produced migrate along the electric gradient and pass through the membrane separating the anode and cathode chamber.

The cathode may be any convenient design that allows good current density and electron transfer to the ETM. Preferably, the cathode is designed to maximize surface area, contact of the liquid phase in the cathode chamber with the cathode, as well as the overall electron transfer characteristics of the cathode.

In one embodiment, the cathode chamber comprises a cathode primarily composed of carbon. This may be a solid piece of carbon that has been machined to have flow-channels or other physical shaping that increases surface area and contact time between the ETM and the cathode.

In another embodiment, the cathode chamber comprises a carbon electrode that is a thin sheet of carbon, carbon felt, or porous carbon. This is commercially known as "carbon paper" and is available under the following brand names, Toray Carbon Paper TGP-H-060, Carbon Paper AvCarb. Other similar products are also available and will be known to those skilled in the art. Multiple sheets of carbon paper, electrically connected, may be used as the cathode and thus provide increased surface area.

In certain embodiments, the cathode chamber is constructed to allow the collection of hydrogen gas in a headspace, or other suitable area, designed to allow small bubbles of hydrogen gas which may adventitiously form on the cathode during normal operation of the EBM to separate from the liquid phase surrounding the cathode, and to allow the removal of the hydrogen gas from the EBM device. This hydrogen gas may be recovered and used as a reagent stream for other chemical processes, or as a fuel.

In various embodiments, the device of the present disclosure will include a proton permeable membrane that separates the anode and cathode chamber. The proton permeable membrane can be, in one embodiment, a modified Nafion® membrane which allows protons (as hydronium ions, $H_3O^+$) to travel across it. The proton permeable membrane may support or contain a catalyst on the anode side, for the production of oxygen gas.

In some embodiments of the present disclosure, the cathode chamber comprises the cathode, and one or more membranes which are located between and separate the cathode from the bulk reaction phase. This separation is enabled by the presence of a polymeric membrane, most typically hydrophilic, for example, polyacrylonitrile, that functions as a physical barrier to retain the optional ETM, the cofactor and the redox enzyme and to prevent these species from dispersing or entering into the bulk reaction phase that circulates within the cathode chamber.

The membrane can have one or more pores extending therethrough. The pores can be used to house the redox enzyme and/or cofactor. This membrane can be "asymmetric", as the size of the pores can have openings that are larger on one side (e.g., the side facing the bulk reaction phase) than on the other side (e.g., the side facing the cathode) of the membrane.

The size of the pores can be expressed as a molecular weight cutoff. For example, a membrane may be called a 10 KDa membrane, meaning that the size of the pore of the side of the membrane where the pore size is smaller is of a size such that molecule having a molecular weight greater than 10 KDa (kilodalton) will not pass through the membrane to any substantial degree. In some embodiments, the pores can have a first opening on a first surface of the membrane facing the cathode, wherein the first opening is sufficiently small to prevent molecules having a molecular weight greater than 100 KDa (e.g., greater than 100 kDa, greater than 80 kDa, greater than 60 kDa, greater than 50 kDa, greater than 40 kDa, greater than 30 kDa, greater than 20 kDa, greater than 20 kDa, greater than 10 kDa, greater than 5 kDa, or greater than 1 kDa) from substantially passing through. The pores can further have a second opening on a second surface of the membrane facing the process stream, wherein the second opening is sufficiently large to permit at least a portion of the redox enzyme contained within the pores to contact the substrate in the process stream. The second opening can be larger in size than the first opening.

Gaskets may be provided as necessary to create interstitial spaces between the one or more membranes, as desired. The bulk reaction phase can be organic in nature, and reasonably immiscible with water. The cathode chamber may be fitted with ports to allow fluids contained in any optional interstitial spaces or compartments to be removed, replaced, or recirculated independently. The asymmetric membrane supports the interfacial contact between the process stream and the aqueous phase containing the redox enzyme, and also with the fluid that is directly the contact with the cathode. The pore size of the asymmetric membrane is preferably chosen to be as large as possible while still preventing the redox enzyme, cofactor and/or ETM from passing through the membrane and/or entering into the process stream to a significant degree. In some embodiments, more than 99%, more than 98%, more than 95%, more than 90%, more than 80%, more than 70%, more than 60%, more than 50% of the redox enzyme, cofactor and/or ETM are retained by the membrane. In certain embodiments, the process stream is substantially free of the redox enzyme, cofactor and/or ETM, e.g., containing less than 50%, less than 40%, less than 30%, less than 20%, less than 10%, less than 5%, less than 2%, or less than 1% of the redox enzyme, cofactor and/or ETM.

One exemplary hydrophilic asymmetric membrane is described in U.S. Pat. Nos. 4,705,704 and 5,077,217, the entire disclosure of both of which is incorporated herein by reference. It should be noted that, however, the membrane is used in U.S. Pat. Nos. 4,705,704 and 5,077,217 to separate the reactant phase containing the substrate and the product phase containing the resulting product. That is, the substrate and product are on different sides of the membrane and thus, are not in the same process stream. In addition, the membrane in U.S. Pat. Nos. 4,705,704 and 5,077,217 must simultaneously effect a migration of the product the enzyme-catalyzed reaction across the membrane contains. Furthermore, the enzymes used therein do not require reducing equivalents, and there is no disclosure of the use of any membrane in connection with any electrochemical process, or for the purpose of preventing ETM or cofactors from mixing with a process stream.

As used herein, the term "bulk reaction phase", or "bulk organic reaction phase" is the liquid or gas or fluid phase in which the substrate and/or the product are dissolved. In standard usage, this liquid or gas or fluid is also termed a "process stream", and those ordinarily skilled in the art will readily understand these terms.

In an embodiment of the present disclosure, the cathode is separated, e.g., by a membrane as disclosed herein, from the bulk organic reaction phase in which the chemical species to be reduced (i.e. the substrate) are present, and in which the reduced product of the reaction will be contained. The bulk organic reaction phase may be continuously circulated as a process stream containing chemical species that are desirable to be reduced by a redox enzyme system. During reaction, the composition of the reaction phase continuously changes as the amount or concentration of the substrate decreases while the amount or concentration of the product increases. At the end of the reaction, the bulk organic process stream contains primarily the resulting product chemical species. As an example of a bulk organic phase, solvents such as heptane, tert-butyl methyl ether, toluene, or other organic solvents that are immiscible with water can be used to provide the necessary solvation of the substrate and the reduced product. It will be immediately appreciated by a person skilled in the art that the bulk organic reaction phase must also be compatible with the material of the asymmetric membrane so as not to compromise or dissolve the membrane.

In an embodiment of the present disclosure, an optional electron transport mediator may be used to transport electrons from the cathode to the cofactor. The ETM is optional because cofactors can directly transport electrons from the cathode to the redox enzyme, without requiring an ETM. In some embodiments, an ETM may be desirable.

ETM, if present in the cathode liquid phase, can be retained by the asymmetric membrane and thus, does not substantially or significantly enter the reaction phase. This can be achieved by possessing a sufficiently high molecular weight (e.g., via chemical modification of the ETM) in the case of an aqueous cathode liquid phase. In the case of a non-aqueous or partially aqueous cathode liquid phase (e.g., organic), the ETM can be chosen to have suitable solubility therein, or the solvent can be chosen to suitably solve the ETM.

In certain embodiments, the ETM and/or the cofactor can be chemically modified by methods such as grafting to a soluble polymer, such that they cannot pass through the pores of the membrane that communicate to the cathode chamber. In this manner, the ETM is held inside the cathode chamber, and the cofactor is held inside the porous matrix of the membrane, even while the aqueous phase in the cathode chamber and the aqueous phase held in the membrane are continuous with each other, thus permitting the ETM to transfer electrons to the cofactor, and hence to the redox enzyme. For example, the ETM and/or cofactor may be covalently linked to a water-soluble polymer that is of a sufficient molecular weight such that it cannot physically move through the smaller pores of the asymmetric membrane. As a specific example, Neutral Red posses a free primary amino group which may be reacted with an activated carboxylic acid group on a polymer such as polyacrylic acid. The covalent linkage could be achieved by the formation of an amide bond between the primary amino group of the Neutral Red and an accessible carboxylic acid group on the polyacrylate. Reagents commonly used for forming amide bonds in aqueous environments, such as conditions encountered during oligopeptide synthesis, may be used, the water-soluble carbodiimides being a common and well-known example of such reagents.

Figure 2:
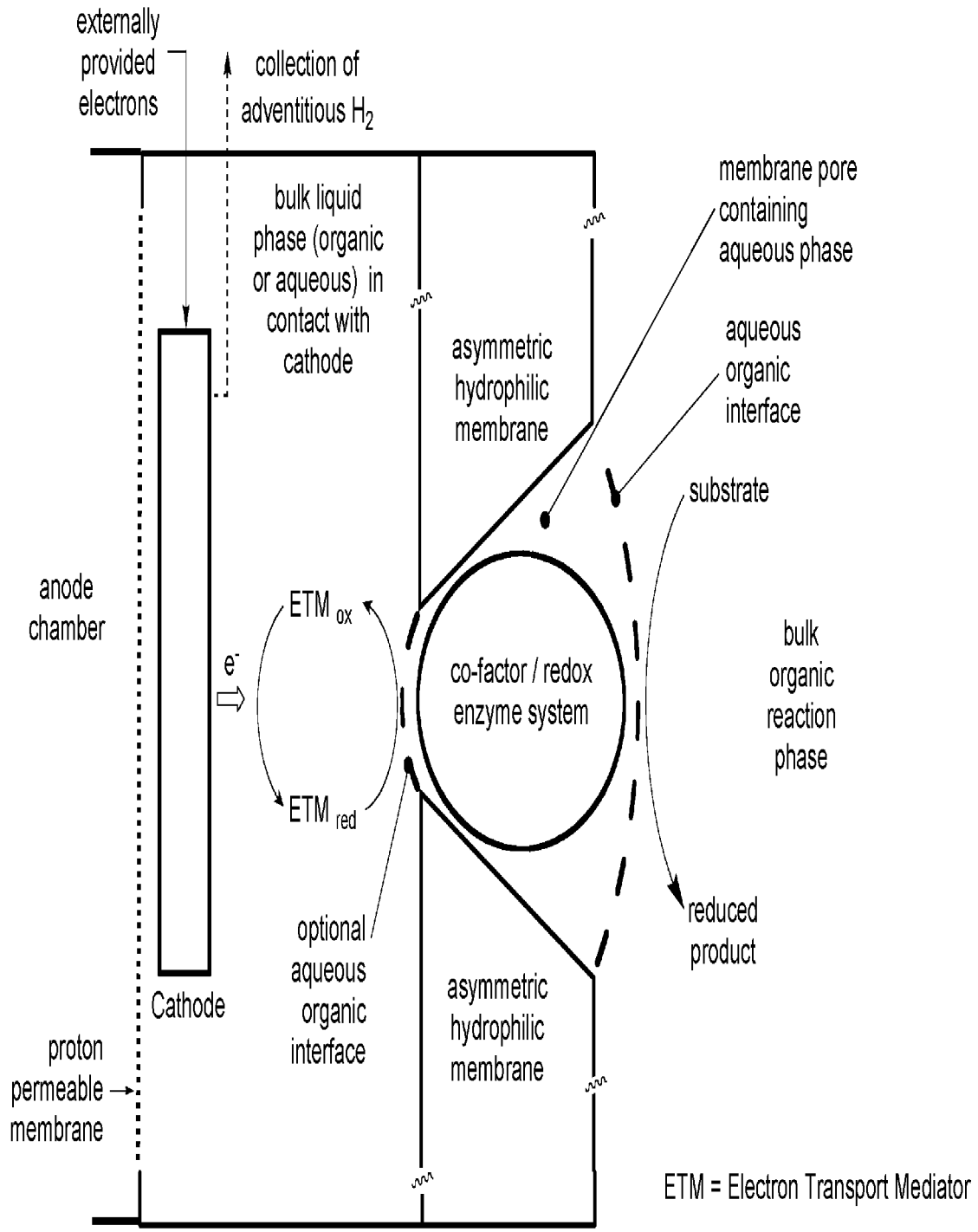
FIG. 2 illustrates, in an exemplary embodiment, a general arrangement of the cathode chamber showing the placement of an asymmetric membrane that separates the cathode and the bulk reaction phase.

In one embodiment, illustrated in FIG. 2, the cathode chamber contains a liquid (aqueous or organic) phase which contains an optional ETM. Electrons are delivered from the cathode to the ETM. A system of redox enzyme or enzymes, optionally together with their required cofactor or cofactors, is contained in a suitable aqueous phase which is held in place by a suitable membrane, most typically a hydrophilic membrane. In one embodiment, a hydrophilic asymmetric membrane is arranged to contain a redox enzyme, or a cofactor/redox enzyme system in an aqueous environment within the porous structure of the membrane. The cofactor accepts electrons from the ETM present in the cathode liquid phase and delivers the electrons to the redox enzyme retained in an aqueous environment in the membrane. The aqueous environment containing the redox enzyme contacts the bulk organic reaction phase, allowing the catalysis of a redox reaction. Both the substrate and the reduced product of the redox reaction are contained in the bulk organic reaction phase.

Referring to FIG. 2, the aqueous phase or environment at the membrane is in direct contact with the liquid phase, which may be aqueous or organic and is in the cathode chamber, and which holds the ETM. The aqueous phase at the membrane containing the redox enzyme is also in contact with the bulk organic reaction phase and separates the bulk organic reaction phase from the cathode. In this embodiment, when the cathode chamber contains an organic phase, the ETM is retained in the cathode chamber by the immiscibility of the organic phase and the ETM in the aqueous phase held by the membrane, and is thus prevented from dispersing into the bulk reaction phase on the other side of the membrane. The cofactor and enzyme present in the aqueous phase held by the membrane is similarly prevented from dispersing into either the cathode chamber or into the bulk organic reaction phase due to its lack of solubility in an organic phase.

Still referring to FIG. 2, the proton permeable membrane on the left separates the cathode chamber from the anode chamber. Hydrogen gas, adventitiously generated at the cathode, may be captured exiting the cathode chamber.

Figure 3:
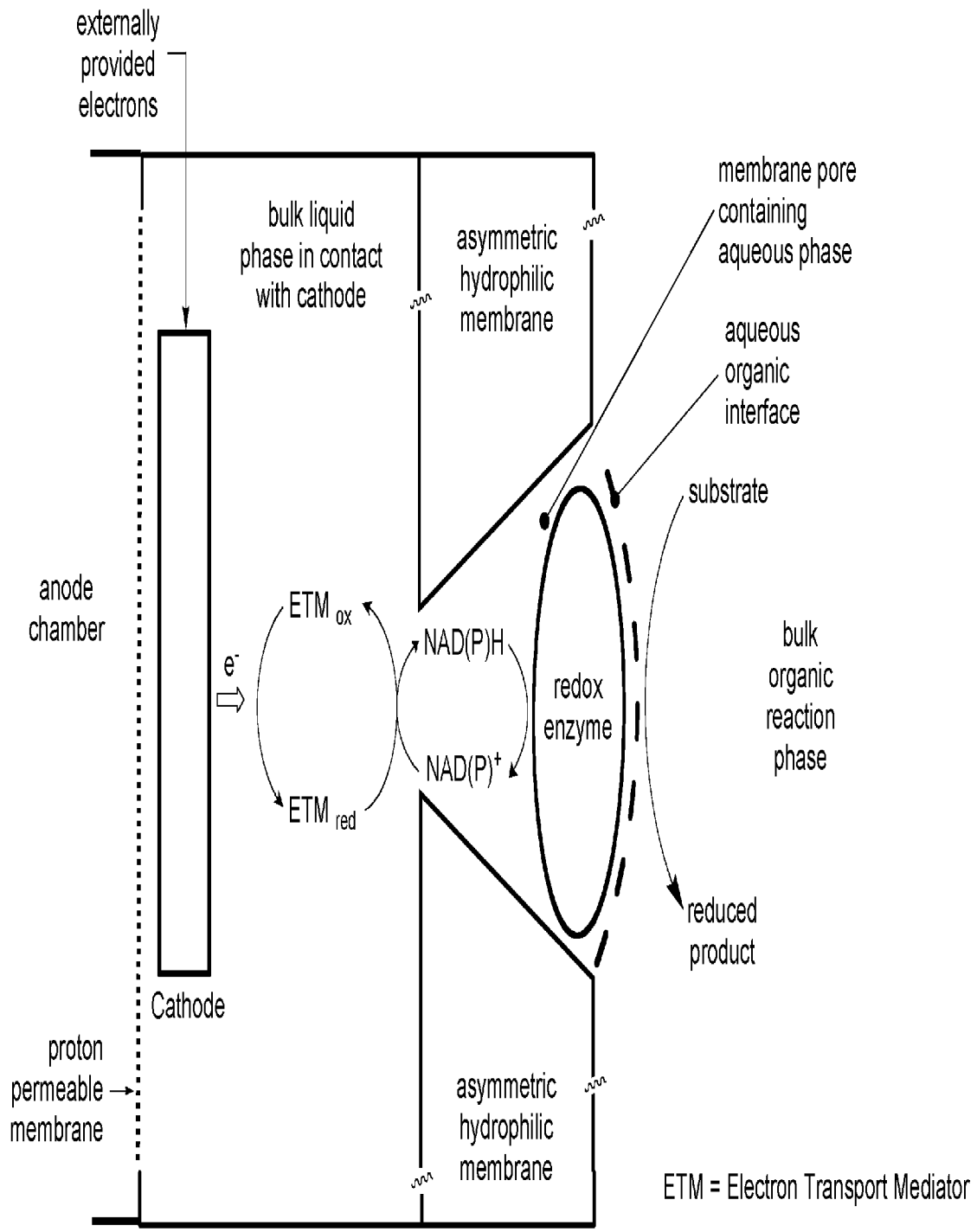
FIG. 3 illustrates, in an exemplary embodiment, use of Neutral Red ("NR") as the ETM in an aqueous bulk phase in the cathode chamber, shuttling electrons to a NAD(P) cofactor/enzyme system contained within the pores of an asymmetric membrane.

In another embodiment, illustrated in FIG. 3, the cathode chamber contains as aqueous phase, and the redox enzyme is prevented from dispersing into the cathode chamber by the size of the pores in the membrane which communicate with the aqueous phase in the cathode chamber. The enzyme system is in an aqueous environment continuous with the bulk aqueous phase in the cathode chamber. The ETM can be appropriately chemically modified to have a molecular weight sufficiently high to be retained in the cathode chamber by the asymmetric membrane. The NAD(P) cofactor in the asymmetric membrane with the redox enzyme may optionally be modified to have a molecular weight sufficiently high to prevent it from leaving the pore of the membrane and entering the cathode chamber. The cofactor/redox enzyme system catalyzes a redox reaction the substrate and product of which remain in the bulk organic reaction phase.

In another embodiment, the cofactor may be unmodified and present in an aqueous phase inside the cathode chamber, while the redox enzyme is retained in the porous structure of the membrane. The cofactor is free to contact the cathode directly, becoming reduced, and then to diffuse through the pores in the membrane to reach the redox enzyme and provide the electrons for the enzyme catalysed reduction of the substrate contained in the bulk organic reaction phase. In this embodiment, no ETM is present, and both the enzyme and the cofactor are prevented from entering the bulk organic phase by their lack of solubility.

In a closely related embodiment, the cofactor required by the redox enzyme is chemically modified to prevent it from passing through the hydrophilic asymmetric membrane, for example, NAD chemically grafted to PEG oligomers of 20 KDa. This allows the use of a bulk organic reaction phase in a solvent is capable of dissolving the unmodified cofactor despite the organic nature of the solvent.

Figure 4:
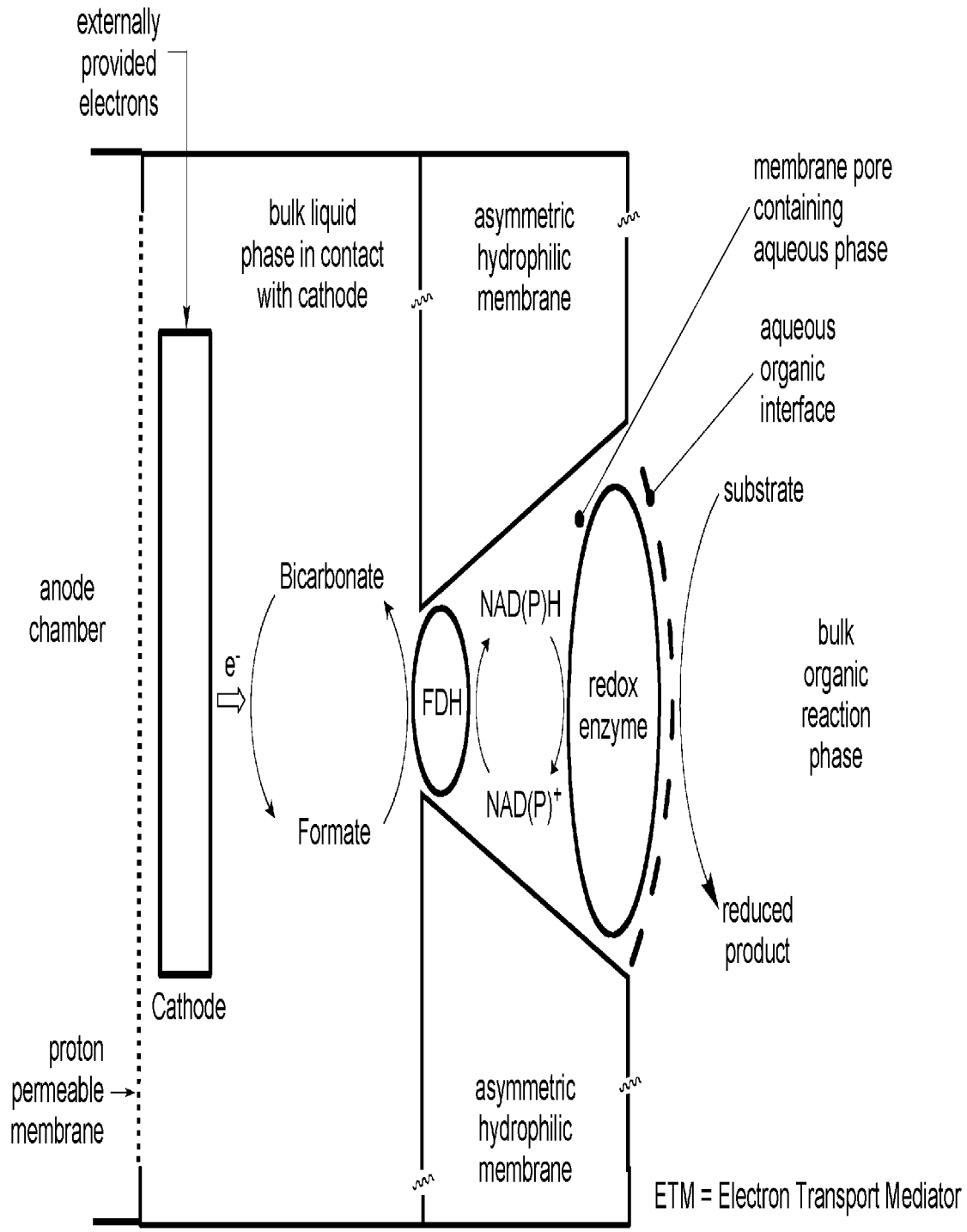
FIG. 4 illustrates, in an exemplary embodiment, use of a formate/carbonate (bicarbonate) couple as the ETM in an aqueous phase in the cathode chamber.
Figure 5:
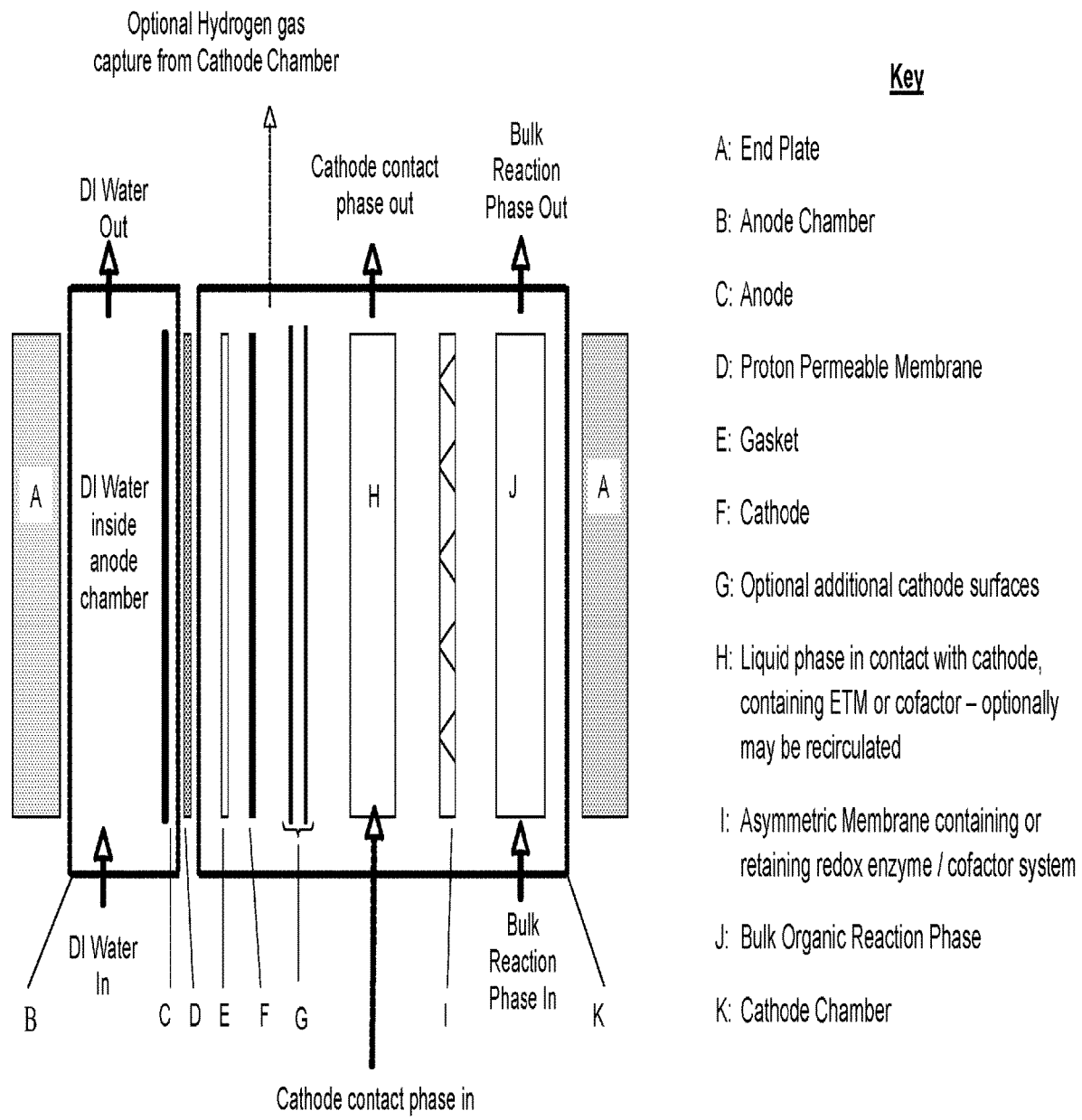
FIG. 5 shows, in an exemplary embodiment, an exploded view of the electrochemical bioreactor with the relative placement of the various components.

In another embodiment, illustrated in FIG. 4, the ETM is a small molecule such as formate, which is capable of delivering reducing equivalents to a redox enzyme system comprising formate dehydrogenase (FDH) itself coupled to a redox enzyme performing the desired reduction of the substrate provided in the continuous process stream. In this operational embodiment, the formate is oxidized by FDH to generate NADH from NAD+, plus bicarbonate, and/or $CO_2$ which may be recaptured as bicarbonate with the optional use of carbonic anhydrase. The NADH is utilized by the redox enzyme reducing the substrate, regenerating NAD+. The bicarbonate is reduced at the cathode to reform formate and complete the cycle. This system in turn catalyzes a redox reaction in the bulk organic reaction phase.

The device of the present disclosure can further comprise an electrochemical cell with integrated instrumentation, that instrumentation comprising anode side oxygen collection system, cathode side gas collection system, flow rate control system, temperature measurement and control system, voltage and current measurement and regulation systems, pH measurement system, dissolved oxygen (DO) measurement system, conductivity measurement system, metabolic activity (fluorescence) measurement systems. Such an integrated system allows the following actions which are of great utility: electron and proton transfer regulation and optimization, microbial side product minimization, $H_2$ gas elimination or minimization, desired product optimization, distilled water (DI) water purity analysis, complete mass balance analysis, flow rate control, temperature control.

In various embodiments, the introduction of reducing equivalents by the EBM to the biological system can include one or more of the following actions:

a) the anode chamber is filled with deionized water, and the cathode chamber is filled with the desired components of the redox enzyme system to which electrons are to be transferred;

b) an external electric current of sufficient voltage (potential) is applied between the anode and the cathode such that water is electrolytically cleaved at the anode causing the flow of electrons into the anode and the formation of neutral oxygen ($O_2$) and positively charged hydronium ions ($H_3O^+$) in the anode chamber;

c) positively charged hydronium ions migrate from the anode chamber towards the cathode chamber through the proton permeable membrane thus providing a source of protons in the cathode chamber;

d) electrons from the anode are driven by an external power source through the external electrical circuit to the cathode;

e) electrons are transferred from the cathode to the desired ETM or redox enzyme cofactor in the cathode chamber;

f) the redox enzyme system performs the desired chemical reduction on the substrate presented in a process stream using the electrons provided from the cathode, either by direct transfer of electrons from the cathode, or directly to a cofactor such as NAD+, or via the transfer of electrons from the cathode to an ETM and then to a cofactor such as NAD+, and then to the redox enzyme; and/or g) protons from the hydronium ions migrating from the anode chamber are disposed into the bulk biological system to balance the electrons that have been transferred from the cathode.

It should be noted that the electricity input of this EBM system could come from a renewable resource (wind, solar, hydroelectric, etc.).

Also provided herein is a method of producing a desired product from a substrate, comprising;

a) providing any of the device disclosed herein with the process stream containing the substrate;

b) applying a suitable voltage from the external power source between the anode and the cathode;

c) accumulating the desired produce in the process stream; and d) optionally, collecting an adventitiously produced hydrogen gas.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Examples

In an example to show the utility of the EBM system for providing reducing equivalents to redox reactions catalyzed by a single, isolated redox enzyme, the reduction of acetophenone to phenethyl alcohol by an alcohol dehydrogenase (EC 1.1.1.1) is performed in the presence of NAD+ cofactor. The alcohol dehydrogenase enzyme and NAD+ that has been chemically modified by covalent attachment to a water soluble polyethylene glycol (PEG) oligomer of 20 KDa are charged into the hydrophilic asymmetric membrane according the manner described in U.S. Pat. Nos. 4,705,704 and 5,077,217. An aqueous solution of Neutral Red, which itself has been modified by covalent attachment to a water-soluble oligomer of polyacrylate is charged to the compartment formed between cathode and the hydrophilic asymmetric membrane. The aqueous phase containing the modified NAD+ (e.g., NAD-PEG) and the alcohol dehydrogenase is continuous with the modified Neutral Red aqueous phase which is contacting the cathode, while an organic phase containing acetophenone is provided on the other side of the hydrophilic asymmetric membrane. A sufficient voltage is applied to cause the reduction of the Neutral Red at the cathode, which subsequently reduces NAD+ to NADH. NADH binds to the alcohol dehydrogenase and reduces the acetophenone to phenethyl alcohol, with the concomitant oxidation of NADH back to NAD+. The hydrophilic asymmetric membrane is sufficiently thin (e.g., 100 microns) that the oxidized NAD+ re-contacts reduced Neutral Red simply via diffusion, and is reduced again to NADH. The solution of Neutral Red can be recirculated independently through the compartment formed between the cathode and the hydrophilic asymmetric membrane, allowing pH control, introduction of more Neutral Red, or passage through a flow-through analytical cell to track overall redox status of the Neutral Red.

EQUIVALENTS

The present disclosure provides among other things novel methods and devices for providing reducing equivalents to biological systems. While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

INCORPORATION BY REFERENCE

All publications, patents and patent applications cited above are incorporated by reference herein in their entirety for all purposes to the same extent as if each individual publication or patent application were specifically indicated to be so incorporated by reference.

What is claimed is:

1. A device for producing a product via a reaction requiring reducing equivalents, comprising:

a. an anode contained in an anode chamber and a cathode contained in a cathode chamber;

b. deionized water in the anode chamber in contact with the anode;

c. a proton permeable membrane that separates the anode and cathode chambers;

d. a liquid phase in the cathode chamber continuously in contact with the cathode, said liquid phase comprising an electron transfer mediator (ETM) capable of transferring reducing equivalents to a redox enzyme system, said redox enzyme system comprising a redox enzyme and a cofactor;

e. a process stream containing a substrate, wherein said substrate, when in contact with the redox enzyme system, can be transformed via catalysis by the redox enzyme system into a desired product; wherein the process stream is an organic phase;

f. a membrane located between the cathode and the process stream, said membrane capable of preventing the ETM and the redox enzyme system from entering into the process stream, wherein the membrane has one or more pores extending therethrough, wherein at least a portion of the redox enzyme system is contained within the pores; and g. an external power source providing a voltage between the anode and the cathode.

2. The device of claim 1 wherein the membrane permits interfacial contact between the liquid phase and the process stream, while preventing mixture of the liquid phase and the process stream and preventing the process stream from contacting the cathode.

3. The device of claim 1 wherein the membrane is a hydrophilic asymmetric membrane having at least a portion of the redox enzyme system contained therein.

4. The device of claim 1, wherein the pores have a first opening on a first surface of the membrane facing the cathode, wherein the first opening is sufficiently small to prevent molecules having a molecular weight greater than 1 KDa from passing through.

5. The device of claim 4, wherein the pores further have a second opening on a second surface of the membrane facing the process stream, wherein the second opening is sufficiently large to permit at least a portion of the redox enzyme contained within the pores to contact the substrate in the process stream.

6. The device of claim 5, wherein the second opening is larger in size than the first opening.

7. The device of claim 1 wherein the co-factor is located in the membrane or in the liquid phase.

8. The device of claim 1, wherein the redox enzyme system is substantially insoluble in the process stream.

9. The device of claim 1, wherein the process stream is substantially immiscible with the liquid phase.

10. The device of claim 1 wherein the liquid phase is recirculated in and out of the cathode chamber.

11. The device of claim 1 wherein the ETM is selected from one or more of Neutral Red, nicotinamide adenine dinucleotide (NAD+), nicotinamide adenine dinucleotide phosphate (NADP+), flavin mononucleotide (FMN), flavin adenine dinucleotide (FAD), ferredoxin, quinone, and humic acid, each optionally chemically modified in a manner to retain their redox properties and functional interaction with redox enzymes while permitting the membrane to prevent the ETM from substantially entering into the process stream.

12. The device of claim 1 wherein the ETM is formate or bicarbonate.

13. The device of claim 1, wherein the redox enzyme system comprises a P450 enzyme, a P450 reductase, and optionally ferredoxin.

14. The device of claim 1, wherein the redox enzyme system comprises a ketoreductase or alcohol dehydrogenase.

15. The device of claim 1, wherein the redox enzyme system performs denitrification.

16. A method of producing a desired product from a substrate, comprising:

a. providing the device of claim 1 with the process stream containing the substrate;
   b. applying a suitable voltage from the external power source between the anode and the cathode, and
   c. optionally, collecting an adventitiously produced hydrogen gas.

17. The method of claim 16, wherein the process stream is a bulk organic phase in which the redox enzyme system is substantially insoluble.

18. The method of claim 16 wherein the ETM is selected from one or more of Neutral Red, nicotinamide adenine dinucleotide (NAD+), nicotinamide adenine dinucleotide phosphate (NADP+), flavin mononucleotide (FMN), flavin adenine dinucleotide (FAD), ferredoxin, quinone, and humic acid, each optionally chemically modified in a manner to retain their redox properties and functional interaction with redox enzymes while permitting the membrane to prevent the ETM from substantially entering into the process stream.

19. The method of claim 16 wherein the ETM is formate or bicarbonate.

20. The method of claim 16 wherein the redox enzyme system comprises a ketoreductase or alcohol dehydrogenase enzyme.

21. The method of claim 16 wherein the redox enzyme system comprises a P450 enzyme, a P450 reductase, and optionally ferredoxin.

22. The method of claim 16 wherein the redox enzyme system performs denitrification.

23. The method of claim 16 further comprising retaining the redox enzyme system and the ETM by the membrane, such that the process stream is substantially free of the redox enzyme system or the ETM.

\* \* \* \* \*